United States Patent [19]

Bellows

[11] Patent Number: 4,509,332
[45] Date of Patent: Apr. 9, 1985

[54] APPARATUS FOR MONITORING CORROSIVE SALT SOLUTIONS IN A LOW PRESSURE STEAM TURBINE

[75] Inventor: James C. Bellows, Maitland, Fla.

[73] Assignee: Westinghouse Electric Corp., Pittsburgh, Pa.

[21] Appl. No.: 605,031

[22] Filed: Apr. 30, 1984

[51] Int. Cl.$^3$ .............................................. F01K 13/02
[52] U.S. Cl. ...................... 60/660; 324/446; 415/118
[58] Field of Search .................. 60/646, 657, 660; 415/118; 324/446

[56] References Cited

U.S. PATENT DOCUMENTS

| 4,339,719 | 7/1982 | Rhines et al. | 326/446 |
| 4,386,498 | 6/1983 | Lee et al. | 60/646 |
| 4,455,530 | 6/1984 | Lee et al. | 415/118 |

Primary Examiner—Stephen F. Husar
Attorney, Agent, or Firm—D. Schron

[57] ABSTRACT

A low pressure steam turbine which is subject to an extremely narrow corrosive salt deposition zone includes rotating and stationary blades. One of the stationary blades has an array of sensors thereon divided up into a plurality of rows, one near the tip of the blade, one near the root of the blade and the third intermediate the two. The sensors are of the type which are flexible so as to conform to the curvature of the blade and will provide an output signal indicative of the presence of a salt solution. The outputs from the sensors are analyzed to provide an indication of the location of the salt solution zone.

12 Claims, 6 Drawing Figures

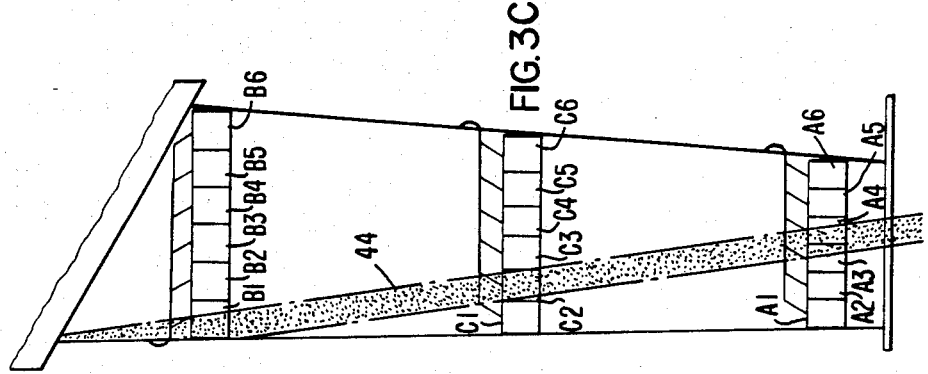
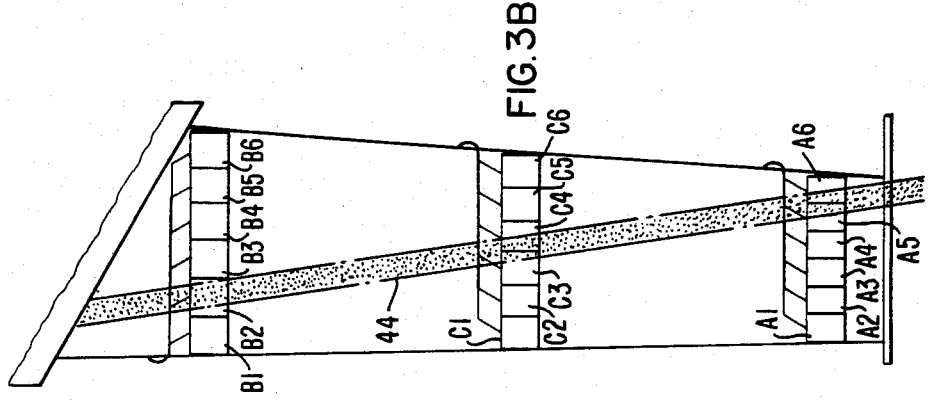
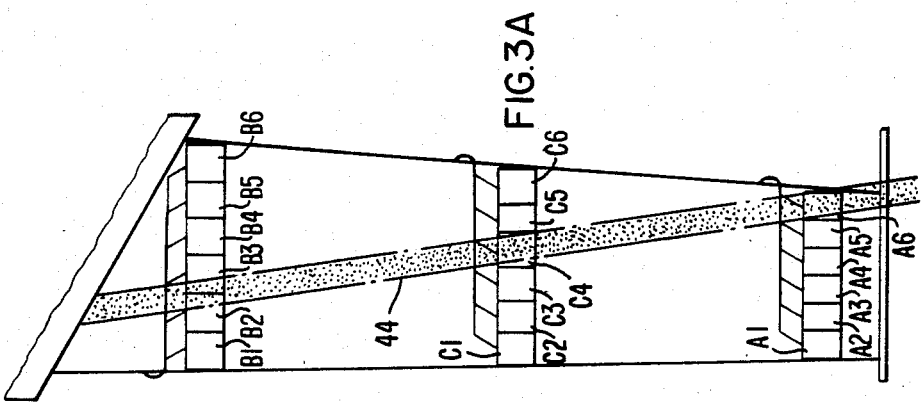

APPARATUS FOR MONITORING CORROSIVE SALT SOLUTIONS IN A LOW PRESSURE STEAM TURBINE

BACKGROUND OF THE INVENTION

1. Field of the Invention

The invention in general relates to steam turbines, and more particularly, to a conductivity sensor array for monitoring purposes.

2. Description of the Prior Art

It is well known that the impurities in steam used to drive steam turbines are a corrosive concern and that deposition of corrosive salt impurities on the rotating turbine blades may lead to stress corrosion cracking failure.

Of particular concern is sodium chloride which, although dissolved in the superheated steam at low concentrations, can deposit at high concentrations as the steam expands through the turbine. Near the exit of the low pressure section of the turbine arrangement, the steam undergoes an expansion whereby a consequent transition from a dry to a wet condition takes place. The entrained sodium chloride could then form a saturated solution which could lead to corrosion and cracking of the rotating blades.

If the location of the salt deposition zone is known, the expansion path of the steam can be modified such that the salt solution deposition can be shifted to a stationary turbine blade. An arrangement for detecting and shifting the zone is described and claimed in U.S. Pat. No. 4,386,498.

The present invention provides for an arrangement by which it is possible to more accurately determine the exact location of the salt solution zone as well as its direction of movement, so as to more accurately deposit the salt solution zone on a stationary turbine blade by manipulation of turbine operating parameters.

SUMMARY OF THE INVENTION

The present apparatus which monitors the corrosive salt solution zone includes a first plurality of sensors which are affixed to a selected one of the stationary blades of the steam turbine, at a first location on the blade. At least a second plurality of similar sensors are affixed to the same stationary blade at a second location on the blade. Each of the sensors are of the type which will provide an output signal indicative of the presence of a salt solution when in contact therewith. An analyzing means responsive to all of the sensor output signals is operable to provide an indication of the location of the salt solution zone so that appropriate action, if at all required, may be undertaken to move the salt solution zone back to the stationary blade should it deviate therefrom.

BRIEF DESCRIPTION OF THE DRAWINGS

FIGS. 3A to 3C illustrate a salt solution zone in relation to the turbine blade of FIG. 2.

DESCRIPTION OF THE PREFERRED EMBODIMENT

A common type of steam turbine system includes a plurality of turbines in the form of a high pressure turbine, an intermediate pressure turbine and a low pressure turbine. The turbines are in a closed loop which includes a steam generator for supplying steam to the high pressure turbine and a condenser which receives the low pressure turbine discharge. Water from the condenser is provided back to the steam generator and is generally treated for removing impurities. A portion of the low pressure turbine is illustrated in FIG. 1 and includes a plurality of turbine blades 10 to 27 with the even numbered blades being connected to rotor 30 and constituting rotor blades, while the odd numbered blades are connected to an inner turbine cylinder and constitute stationary blades.

In a typical operation, superheated dry steam enters the first stage (constituted by blades 26 and 27) and passes through subsequent stages where expansion and temperature and pressure changes take place. At approximately the last stage (constituted by blades 10 and 11) or the next to last stage (constituted by blades 12 and 13) and depending upon operating conditions, there is a transition zone where the dry steam converts to a moist fog-like condition and any entrained sodium chloride precipitates out into a relatively narrow salt solution zone or band which can cause stress corrosion and cracking problems. The salt solution zone shifts under different operating conditions and upstream of the zone, dry solid sodium chloride is stable in the presence of superheated steam and does not have the corrosive effects, whereas downstream of the zone in the wet region, the salt contamination is so dilute that it has no corrosive effects. By controlling the operating conditions of the turbine, the salt solution zone may be shifted to a stationary blade where the stress corrosion effects are minimized, as brought out in the aforementioned patent.

In the present invention the position of the salt solution zone relative to a stationary blade may be ascertained with a greater degree of accuracy than in the referenced patent and in addition, the general width and shape as well as the direction of any movement of the salt solution zone may be determined.

Figure 1:
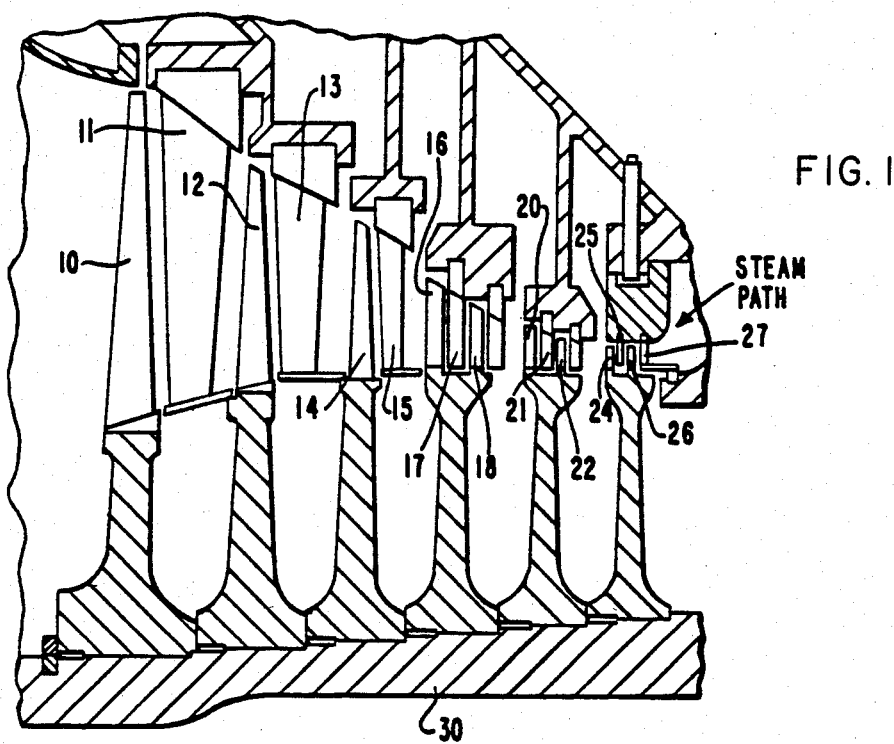
FIG. 1 is a cross-sectional view through a portion of a typical low pressure steam turbine.
Figure 2:
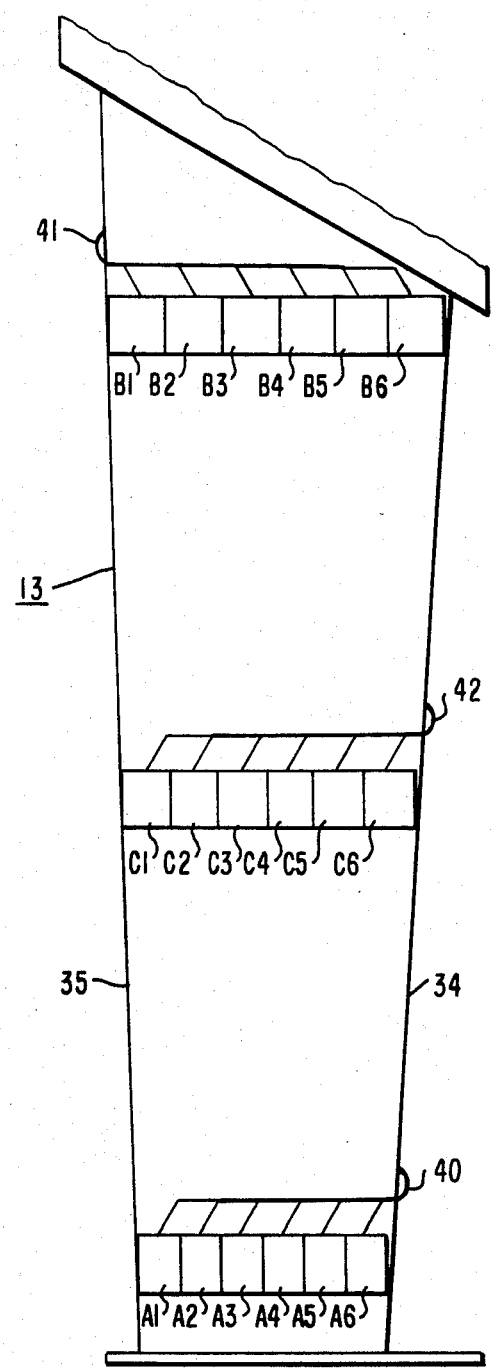
FIG. 2 is an isolated view of one of the stationary turbine blades of FIG. 1 illustrating the placement of various sensors thereon.

An arrangement for providing knowledge relative to the salt solution zone is illustrated in FIG. 2 which is an isolated view of stationary blade 13 of the next to last stage of the turbine of FIG. 1. A first plurality of sensors in the form of conductivity sensors A1 to A6 is affixed to the turbine blade near the tip thereof between the leading edge 34 and trailing edge 35. Each of the sensors is of the type which will provide an output signal indicative of the presence of a salt solution. The sensors are flexible in order to conform to the curvature of blade 13 and are fabricated to withstand the hostile environment inside the turbine. One such type of sensor which may be utilized herein is described and claimed in copending application Ser. No. 363,757 filed Mar. 30, 1982, now U.S. Pat. No. 4,455,530, and assigned to the same assignee as the present invention, and hereby incorporated by reference.

Individual electrical connections to the sensors may be conducted via a common cable 40 to appropriate analyzing equipment. In a preferred embodiment, the sensors are aligned in a row with adjacent sensors touching one another.

Another identical plurality of sensors B1 to B6 is provided with each sensor being affixed to the turbine blade 13 in the vicinity of the root thereof. Sensors B1 to B6 conform to the curvature of blade 13 and are aligned in a row touching one another. Due to the greater dimension of the blade, near the root, sensors B will be slightly wider than sensors A. Electrical connections to the individual sensors are collectively provided to the analyzing equipment by means of cable 41.

In order to provide for a more accurate reading with respect to the location of the salt solution zone, the arrangement of FIG. 2 additionally includes a third plurality of sensors C1 to C6 positioned on the turbine blade 13 between the first and second pluralities previously described. Sensors C1 to C6 are similar to the other sensors and are aligned in a row touching one another with electrical connections being made via cable 42.

FIG. 3A reproduces blade 13 with the affixed plurality of sensors and additionally shows a representative salt solution zone 44, the exact width and shape of which depends upon the blade contour as well as velocity, pressure and temperature conditions at the blade.

In FIG. 3A it is seen that the salt solution zone 44 contacts sensor A6 of the first plurality, sensors B2 and B3 of the second plurality and sensor C4 of the third plurality. These sensors will provide individual output signals indicative of high conductance while the remaining sensors will provide output signals indicative of low or no conductance. With this information communicated to analyzing equipment, the location of the particular salt solution zone 44 may be established.

In FIG. 3B, the salt solution zone 44 has moved such that sensors A5 and A6, C3 and C4 and B2 provide the high conductance output signals and in FIG. 3C with further movement of salt solution zone 44, the high conductance output signals will be provided by sensors A3 and A4, C2 and B1.

Figure 4:
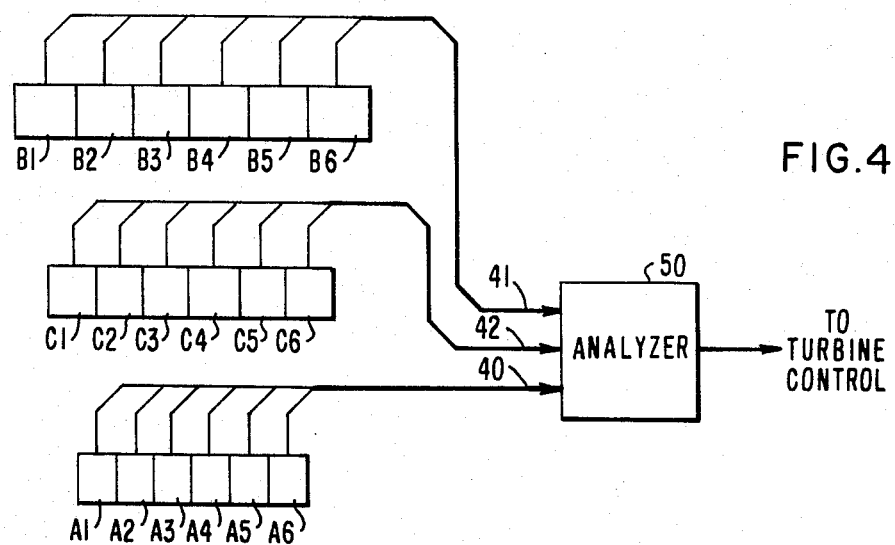
FIG. 4 is a block diagram illustrating the cooperation between the sensors of FIG. 2 and analyzing equipment.

In FIG. 4 the sensors A1 to A6, B1 to B6 and C1 to C6 are shown connected via their respective cables 40 to 42 to analyzer equipment 50. Analyzer 50 is operable to register which of the sensors, if any, are providing output signals so that this information may be communicated to an operator. Additionally, and as indicated by connection 51, the results of the analysis may be provided to process control equipment (not shown) for moving the salt solution zone as described in the referenced patent.

The recordation of which sensors are providing output signals may be utilized to visually display the general location of the salt solution zone. In addition, any subsequent response of neighboring sensors will provide an indication of directional movement of the salt solution zone such that if it proceeds toward a rotating blade, proper corrective action may be taken to again move it back to the stationary blade. In this respect it is noted that although one stationary blade of the next to last stage is illustrated as having the array of sensors, it is within the scope of the present invention to provide a similar such array on other stationary blades such as 11 or 15.

I claim:

1. Apparatus for monitoring corrosive salt solutions in a low pressure steam turbine having stages of rotating and stationary blades, said solutions occurring in a relatively narrow salt solution zone at one of the ultimate stages of said turbine, comprising:
   (A) a first plurality of sensors affixed to a selected one of said stationary blades at a first location on said blade;
   (B) at least a second plurality of sensors affixed to said selected stationary blade at a second location on said blade;
   (C) each of said sensors of said first and second plurality being of the type which will provide an output signal indicative of the presence of a salt solution; and
   (D) means responsive to all said sensor output signals to provide an indication of the location of said salt solution zone.

2. Apparatus according to claim 1 wherein:
   (A) the sensors of said first plurality are aligned in a row.

3. Apparatus according to claim 2 wherein:
   (A) each sensor of said first plurality touches its adjacent sensor.

4. Apparatus according to claim 2 wherein:
   (A) said row is located near the tip of said stationary blade.

5. Apparatus according to claim 1 wherein:
   (A) the sensors of said second plurality are aligned in a row.

6. Apparatus according to claim 5 wherein:
   (A) each sensor of said second plurality touches its adjacent sensor.

7. Apparatus according to claim 5 wherein:
   (A) said row is located near the root of said stationary blade.

8. Apparatus according to claim 1 wherein:
   (A) said first plurality of sensors extends between the leading edge and trailing edge of said stationary blade.

9. Apparatus according to claim 8 wherein:
   (A) said second plurality of sensors extends between the trailing edge and leading edge of said stationary blade.

10. Apparatus according to claim 1 which includes:
    (A) a third plurality of said sensors affixed to said stationary blade at a position between said first and second pluralities.

11. Apparatus according to claim 10 wherein:
    (A) the sensors of said third plurality are aligned in a row.

12. Apparatus according to claim 1 wherein:
    (A) said stationary blade is in the next to last blade stage of said turbine.

* * * * *